US008246937B2

(12) United States Patent
Robinson et al.

(10) Patent No.: US 8,246,937 B2
(45) Date of Patent: Aug. 21, 2012

(54) HAIR AND SKIN CARE COMPOSITION

(75) Inventors: Freda E. Robinson, Nyack, NY (US);
Kenneth Buckridge, Mahwah, NJ (US);
Leona Giat Fleissman, Ridgewood, NJ (US)

(73) Assignee: Avon Products, Inc., New York, NY (US)

( * ) Notice: Subject to any disclaimer, the term of this patent is extended or adjusted under 35 U.S.C. 154(b) by 2359 days.

(21) Appl. No.: 10/885,166

(22) Filed: Jul. 6, 2004

(65) Prior Publication Data

US 2006/0008437 A1    Jan. 12, 2006

(51) Int. Cl.
*A61K 8/00* (2006.01)

(52) U.S. Cl. ............ 424/70.1; 424/70.11; 424/70.12; 424/70.27; 424/70.28

(58) Field of Classification Search .................. None
See application file for complete search history.

(56) References Cited

U.S. PATENT DOCUMENTS

| 3,935,868 | A | | 2/1976 | Zeffren et al. | |
|---|---|---|---|---|---|
| 3,964,499 | A | | 6/1976 | Wajaroff et al. | |
| 4,690,821 | A | * | 9/1987 | Smith et al. | 424/401 |
| 4,837,019 | A | * | 6/1989 | Georgalas et al. | 424/59 |
| 4,960,845 | A | | 10/1990 | O'Lenick et al. | |
| 5,302,378 | A | * | 4/1994 | Crotty et al. | 424/59 |
| 5,393,519 | A | | 2/1995 | Dowell et al. | |
| 5,519,063 | A | * | 5/1996 | Mondet et al. | 514/772.4 |
| 6,211,125 | B1 | | 4/2001 | Crudele et al. | |
| 6,468,515 | B1 | * | 10/2002 | Uchiyama et al. | 424/70.27 |
| 6,709,648 | B2 | * | 3/2004 | Sako et al. | 424/70.12 |
| 6,821,509 | B2 | * | 11/2004 | Soane et al. | 424/70.11 |
| 2003/0165454 | A1 | | 9/2003 | Snyder et al. | |
| 2007/0281048 | A1 | * | 12/2007 | Miljkovic | 424/776 |

OTHER PUBLICATIONS

Hair Care Ingredients, Household & Personal Product Industry, Dec. 2003.*
Schercemol PDD Ester technical data sheet, accessed online Jun. 15, 2011.*
Hair Care Ingredients, Household & Personal Products Industry, Dec. 2003.*
Schercemol PDD Ester technical data sheet, accessed online Jun. 15, 2011.*

* cited by examiner

*Primary Examiner* — Anand Desai
*Assistant Examiner* — Melissa Mercier
(74) *Attorney, Agent, or Firm* — Joan M. McGillycuddy; Charles J. Zeller; David M. Joyal

(57) ABSTRACT

The present invention provides cosmetic compositions that form a durable film or coating on surfaces such as hair or skin. The compositions of the invention comprise one or more anionic silicones and one or more high molecular weight esters, the combination of which provides a durable film. Methods for treatment of hair and skin employing the compositions of the invention are also provided.

17 Claims, No Drawings

HAIR AND SKIN CARE COMPOSITION

FIELD OF THE INVENTION

The present invention relates to cosmetic compositions. More particularly, the invention relates to compositions that form a durable film or coating on surfaces such as hair or skin.

BACKGROUND OF THE INVENTION

Human hair varies greatly in character between individuals. Hair differs in thickness, texture, color and shape. A variety of products and methods have been developed to modify each of these characteristics. There are hair coloring products, hair conditioning products, hair cleansers and products to control the straightness or curliness of hair. This last category of hair products is the subject of the present invention.

Natural curly hair or frizzy hair frequently causes many hair styling problems. For example, the hair tends to spread uncontrollably, hair tips curl up, and/or it is difficult to be arranged tidily. A number of methods have been proposed for curing these problems of curly or frizzy hair. A typical cure is the so-called permanent straightening treatment, a chemical treatment which comprises fully cleaving disulfide bonds in hair keratin through a chemical reduction process and stretching the hair by adhering it to a panel or combing it. The straightened hair is then oxidized and fixed to restore the disulfide bonds in the hair, thereby permanently straightening the hair. The disadvantage of this approach is that the harsh chemicals used are an irritation to the scalp and skin due to the high pH (10-12) of the caustics or similar compounds. In addition, the hair cuticle is uplifted causing extensive damage which results in dry and dull hair from reduced sebum flow from the scalp. The structure of the hair is also permanently damaged because the chemical bonds in the hair fibers are broken and only some are reformed into new covalent bonds.

An alternative solution is the use of hair spray products. Hair spray products are applied to wet or dry hair and contain a polymer, or mixtures of polymers, that remain fixed on the previously styled hair. The film-forming polymers are used to provide a flexible sheath on the shaped hair after drying, and, therefore, for mechanical reasons, retard the return of each individual hair to its natural shape. In addition, the polymeric film provides an overall stiffening of the hair. The hair behaves as if the individual hair strands are welded together, and the final hairstyle has better cohesion, therefore, resisting the natural forces that return the hair to its natural shape. A disadvantage of the conventional hair sprays is that the polymer film is easily removed by a single shampoo requiring that the hair spray be reapplied. Additionally, polymer films lose their effectiveness to retain the style of the hair over time, especially when exposed to high relative humidity.

It is an object of the present invention to provide a composition that is able to straighten hair without the damaging disruption of chemical bonds in the hair and is also durable by remaining on the hair even after shampooing and exposure to high humidity.

SUMMARY OF THE INVENTION

It has been found that a mixture of an anionic dimethicone and a high molecular weight ester, when applied to hair, provides a synergistic straightening effect that is highly durable and water resistant. Further, this straightening effect occurs without damaging the hair by disrupting chemical bonds in the keratin structure of the hair. Dampened hair treated with the mixture relaxes, allowing it to straighten. When the mixture dries, a film is left on the hair which provides a structural stiffness to the hair fiber maintaining its straightened shape. This film is durable and water resistant maintaining the structural stiffness even after multiple shampoos or exposure to at least 90% relative humidity for at least 8 hours.

In addition to the performance characteristics, the mixture of an anionic dimethicone and a high molecular weight ester impart consumer acceptable tactile properties as well as other acceptable organoleptics, which are not present when either component of the mixture is used alone. In addition, the mixture can be used with other hair care and skin care ingredients known in the art to improve solubility, manageability, provide emollient functionality and optimize rheology.

It is an object of the invention to provide a hair care composition for the styling of hair that comprises one or more anionic silicones mixed with one or more high molecular weight esters in a cosmetically acceptable vehicle containing hair care and skin care ingredients known in the art for improving solubility, manageability, to provide emollient functionality, and to optimize rheology. Such vehicles include aerosols, creams, emulsions, gels, aqueous solutions, alcohols, lotions, mousses, patches, pomades, powders, solids, sprays, sticks, towelettes, mascara, shampoo or body wash. In one embodiment of the invention, the anionic silicones comprise from about 0.05% to about 20% by weight of the composition and the high molecular weight esters comprise from about 0.1% to about 15% by weight of the composition.

In a more preferred embodiment, the anionic silicones comprise from about 0.1% to about 10% by weight of the composition and the high molecular weight esters comprise from about 0.5% to about 10% by weight of the composition.

In a further embodiment of the invention, the styling effect of the composition lasts for at least about 8 hours and may exceed about 18 hours. In another embodiment, the styling effect remains after at least one, preferably two shampoos. In a preferred embodiment the styling effect of the composition remains after exposure of the hair to at least about 90% humidity for at least about 8 hours, more preferably for at least 18 hours at 90% humidity, and most preferably for at least 24 hours at 90% humidity.

Another embodiment of the invention provides for a method of styling hair comprising optionally wetting the hair then applying a hair care composition comprising one or more anionic silicones and one or more high molecular weight esters. The hair styling composition further comprises a vehicle that may contain one or more adjuvants selected from the group consisting of emulsifiers, emollients, rheology modifiers, solvents, conditioning agents, shine modifiers, film forming polymers, and excipients suitable for use in a hair care product, combing or brushing the hair until the desired shape is achieved, and drying the hair.

A further embodiment of the invention is for the delivery of active agents to the skin or hair to effect a treatment of the skin or hair with an active agent. In this embodiment the invention provides a method comprising applying to the skin or hair a composition comprising one or more anionic silicones, one or more high molecular weight esters, one or more active agents, and a vehicle containing one or more adjuvants selected from the group consisting of emulsifiers, emollients, rheology modifiers, conditioning agents, solvents, film formers, and excipients suitable for use in a skin or hair care product, and drying the skin or hair.

DETAILED DESCRIPTION OF THE INVENTION

As used herein the terms of art are intended to their ordinary and accustomed meaning unless otherwise indicated. All percentages used herein are by weight of the composition unless otherwise indicated. All ingredient concentrations are "as is" unless indicated to the contrary.

By the term "styling effect" we mean the ability of a hair care composition to cause the hair to maintain a different shape than the natural shape of the hair. By the term "long lasting" we mean a time period of at least 8 hours, and preferably in excess of at least 18 hours. By the term "high humidity" we mean relative humidity of 90% at an ambient temperature of at least 68° C. By the term "substantially remains" we mean that sufficient film remains on the hair fiber to retain the desired styling effect. By the term "substantially straighter" we mean that the natural curl or wave of the hair fiber is measureably reduced. By the term "active agent" we mean any ingredient for use in a cosmetic composition that provides a benefit to the hair or skin, and is not present merely as an inert substance used as a diluent or vehicle. Skin care cosmetic active agents provide a cosmetic benefit to the skin, including improving the appearance of skin, protecting the skin, maintaining the skin in good condition, or applying a personal hygiene product to the skin. Pharmaceutic agents may be over the counter and prescription, and provide a benefit in the treatment of a medical condition or disease. Skin means human skin, lips and nails. Hair includes eyelashes. Hair care cosmetic active agents provide a cosmetic benefit to hair, including improving the condition of hair, its shine, the strength of the hair fiber, or its cleanliness.

The present invention relates to a novel combination of one or more anionic silicones and one or more high molecular weight esters to provide a durable film on skin or hair. It has been found surprisingly that the use of this combination provides a straightening effect to hair that is resistant to shampooing and high humidity and is long lasting. In addition this straightening effect is achieved without damaging the hair by treatment with harsh chemicals.

Anionic Silicones

The anionic silicones used in the invention can be any one of several commercially available anionic dimethicones. The anionic dimethicones of the present invention are clear to hazy liquids that are soluble or at least dispersible in water and typically have a viscosity of from about 25 to about 5,000 cps., preferably about 50 to about 2000 cps. These include but are not limited to dimethicone PEG-7 sulfate, dimethicone PEG-7 phosphate, dimethicone PEG-7 phthalate, dimethicone PEG-7 succinate and dimethicone PEG-8 phosphate. A preferred anionic silicone is dimethicone PEG-7 sulfate sold as Ultrasil SA-1 Silicone by B. F. Goodrich, optionally in combination with dimethicone PEG-8 phosphate sold as Ultrasil PE-100 Silicone sold by Goodrich. These anionic silicones are typically present in the composition at a concentration of between about 0.05% by weight and about 20% by weight. More preferably, they are present at about 0.1% to about 10%, most preferably from about 0.5% to about 6%.

High Molecular Weight Esters

The high molecular weight esters of the invention are typically hydrophobic materials, and hence not readily dispersible in water. Typically, they have a molecular weight of above about 450, preferably above about 500, and most preferably a molecular weight of from about 600 to about 3000. The hydrophilic-lipophilic balance (HLB) of the high molecular weight esters of the present invention is typically less than about 8, preferably less than about 6. Suitable esters of the present invention include the di- and tri-esters of dimer and trimer acids, especially those having a polyglyceryl functionality. Suitable commercially available esters include but are not limited to diisostearyl polyglyceryl-3 dimer dilinoleate, diisostearyl polyglyceryl-3 dimer dilinoleate, triisostearoyl polyglyceryl-3 dimer dilinoleate, diisostearyl dimer dilinoleate, triisostearyl trilinoleate, diisostearyl dimer dilinoleate and myristyl lactate. A preferred ester is diisostearyl polyglyceryl-3 dimer dilinoleate sold as Schercemol PDD by Scher Chemicals, Inc. These esters are present in the composition at a concentration of between about 0.1% and about 15% by weight, preferably they are present at about 0.5% to about 10%, most preferably from about 1 to about 8%.

In a particularly preferred embodiment, the weight ratio of the high molecular weight ester to the anionic silicone is from about 5:1 to about 0.5:1, especially about 2.5:1 to 1:1, and most especially 2.25:1 to 1.5:1.

It has been found that an anionic silicone of the present invention, when incorporated in a cosmetic composition together with a high molecular weight ester described above, forms on the hair or skin a quite durable film coating that resists removal by water. Suprisingly, the film as applied also resists removal when exposed to a more hostile environment, for example during shampooing where the hair is washed with a composition containing an anionic surfactant. Additionally, the film resists the effects of humidity, which typically causes hair to curl due to the absorption of moisture by the hair shaft. On hair, these benefits are obtained along with the additional benefits of superior wet combing and dry combing. When, used in a skin care product the film resists humidity, and also resists removal, for example, when the skin is exposed to water, i.e., during bathing, swimming, rinsing, perspiring, etc. Accordingly, the compositions of the present invention are especially useful wherever a water resistant film is desired.

In particular, the finding that dampened hair is found to relax when the compositions of the invention is applied to hair coupled with the ability of the film coatings obtained by the compositions of the present invention to resist humidity make the compositions especially useful as a hair straightening composition, as described in greater detail below.

Other Ingredients

The anionic silicones and the ester emollients can be formulated with a great variety of hair care and skin care adjuvants known to the art that provide an intended functionality. Suitable ingredients include surface active agents as emulsifiers, foam boosters, hydrotropes, solubilizing agents, and suspending agents; solvents; humectants; viscosity control agents and rheology modifiers; chelating agents; film formers; plasticizers; pH adjusters; preservatives; and fragrances. Suitable materials to provide the above identified functions are identified in the International Cosmetic Ingredient Dictionary and handbook, v. 4, Section 4 ($9^{th}$ Edition, 2002) (hereinafter INCI), incorporated herein by reference. For example, suitable emulsifiers include but are not limited to anionic and nonionic surfactants such as Crodafos CS-20 Acid, a mixture of cetearyl alcohol, ceteth-20 phosphate, and dicetyl phosphate sold by Croda, Inc. Rheology modifies which may be used include acrylates, carboxymethylcellulose and hydroxyethylcellulose. Solvents include water, C1 to C6 mono- and polyhydric alcohols, low molecular weight hydrocarbon oils, and the like. Other ingredients which may be used include regular or quaternized silicones, cyclic and linear elastomer suspensions, silicone amino elastomer emulsion, natural or synthetic oils such as squalene or isododecane, mineral oil or petrolatum. These compounds are used in the amount necessary to achieve the intended function and generally range from about 0.01% to about 25% by weight, depending on the nature and purpose of the adjuvant.

Active Agents

In some embodiments of the invention the composition is used to deliver active agents to the skin or hair. Active agents for use with the invention can include but are not limited to hair conditioning agents, skin conditioning agents, hair colorants, bleaching agents, antidandruff agents, hair fixatives, film formers, surface active agents, reducing agents, antibacterials, antifungals, antioxidants, sunscreens, retinoids, alpha-hydroxy acids, beta-hydroxy acids, analgesics, anti-allergenic agents, anti-inflammatory agents, anti-irritants, anti-acne agents, antiseptics, and insect repellants. Suitable materials are identified in INCI.

Cleansing agents for hair and skin are typically anionic, nonionic, and amphoteric surface active agents, for example, fatty acid sulfates such as sodium lauryl sulfate and sodium laureth-2 sulfate, succinates such as disodium stearylsulfosuccinate, isethionates, etc, ethoxylated fatty acid and alcohols, and amides. Other suitable materials are identified in INCI.

Hair conditioning agents include cationic surfactants and quaternary ammonium compounds, including quaternized polymer compounds. Suitable conditioners are identified in INCI at p. 2912 et seq.

Sunscreen agents can be organic sunscreens, which include but are not limited to aminobenzoic acid, avobenzone, cinoxate, dioxybenzone, homosalate, menthyl anthranilate, octocrylene, octyl methoxycinnamate, octisalate, oxybenzone, padimate O, phenylbenzimidazole, sulfonic acid, sulisobenzone, and trolamine salicylate. Sunscreen agents may also be inorganic compounds, which include but are not limited to zinc oxide and titanium dioxide.

Insect repellents include N,N-diethyl-meta-toluamide (DEET), 3-[N-Butyl-N-acetyl]-aminopropionic acid ethyl ester, oil of citronella or any other compound approved by the United States Environmental Protection Agency for use as an insect repellent.

Skin protectants are oils, emollients and occlusives that provide a moisturizing benefit to the skin or that prevent the evaporation of moisture form the skin. Especially useful with the compositions of the present invention are water dispersible esters including but not limited to polyglyceryl-3 laurate, PEG-7 glyceryl cocoate, PEG/PPG-8/3 laurate, and sucrose laurate. Other useful emollients are dimethicone, dimethicone copolyol, isopropyl myristate, isocetyl stearate and diisopropyl adipate.

Antimicrobial agents include but are not limited to alcohol, benzalkonium chloride, benzethonium chloride, hydrogen peroxide, methylbenzethonium chloride, phenol, poloxamer 188, and povidone-iodine. Suitable antifungal agents include but are not limited to calcium undecylenate, providone-iodine, undecylenic acid and zinc undecylenate.

Use of the Composition

The present invention provides a method for styling hair. The method comprises wetting the hair with water or the hair care composition, combing or brushing the hair so that the hair takes on the proper style and drying the hair, typically with a device such as a blow dryer or other heat appliances such as a flat iron, pressing comb, or thermal brush. In a preferred embodiment the hair is combed or brushed with the simultaneous use of a blow dryer so that the heat of the blow dryer can assist the hair in assuming the desired style.

The present invention also provides a method for delivering active agents to the skin or hair. In this embodiment the composition containing the active agent is applied to the skin or hair and allowed to air dry so that the active agent is deposited on the skin and is protected from moisture and abrasion and thereby providing the beneficial effects of the active agent for a longer period of time. Illustrative personal care products include shampoos, hair conditioners, hair shine products, hair colorants, hair straighteners, hair detanglers, antidandruff products, depilatories, exfolliants, sunscreens, insect repellants, skin care products such as moisturizers, toners, etc., antiperspirants and deodorants, make up products, body wash products, products for the lips such as lip liners, lipsticks and lip gloss, mascaras, suntan products, face masks, nail products, and hair sprays.

Methods of Manufacture

The compositions of the present invention are made using conventional methods known to those of ordinary skill in the art. For example in the case of an aqueous emulsion the components of the water phase is added to a vessel with an agitator and mixed until uniform. A premix of the anionic silicone and high molecular weight ester is made in a separate vessel, which premix also includes the other oil phase components. The oil phase is then added to the water phase with agitation until uniform. The remaining ingredients are then added with mixing until uniform. Lastly, the composition is neutralized and thickened with basic solution, with continued mixing.

EXAMPLES

Illustrative examples of the compositions of the present invention are set forth below.

Example 1

| Leave-On Hair Straighter Treatment | |
| --- | --- |
| | Weight % |
| Acrylates/C10-C30 Alkyl Acrylate Crosspolymer | 0.5 |
| Diisostearoyl Polyglyceryl-3 Dimer Dilinoleate | 8.0 |
| Conditioning silicone | 3.0 |
| Low molecular weight emollient esters | 6.0 |
| Ammonium dimethicone PEG-7 sulfate/AQ[1] | 15.0 |
| Aminomethyl Propanol 95% | 0.5 |
| Preservative | 0.14 |
| Fragrance | 0.5 |
| Demineralized Water | QS 100% |

[1]Ultrasil SA-1 from Noveon, Inc. (35% active)

Example 2

| Leave-On Hair Straightener Treatment | |
| --- | --- |
| | Weight % |
| Acrylates/C10-30 Alkyl Acrylate Crosspolymer | 0.6 |
| Diisostearoyl Polyglyceryl-3 Dimer Dilinoleate | 7.5 |
| Low molecular weight emollient esters | 1.0 |
| Conditioning silicone | 0.4 |
| Dimethicone PEG-8 Phosphate[1] | 2.0 |
| Ammonium Dimethicone PEG-7 Sulfate/AQ[2] | 3.0 |
| Silicone fluid | 0.467 |
| Fragrance | 0.6 |
| Silicone elastomer aqueous suspension[3] | 2.5 |
| Cationic surfactant | 0.01 |

-continued

Leave-On Hair Straightener Treatment

| | Weight % |
|---|---|
| Preservative | 0.14 |
| Triethanolamine | 0.55 |
| Demineralized Water | QS 100% |

[1]Ultrasil PE-100 available from Noveon, Inc. (100% active)
[2]Ultrasil SA-1 from Noveon, Inc. (35% active)
[3]67% active Shampoo Composition

| | Weight % |
|---|---|
| Acrylates/C10-C30 Alkyl Acrylate Crosspolymer | 0.5 |
| Diisostearoyl Polyglyceryl-3 Dimer Dilinoleate | 1.6 |
| Low molecular weight ester emollients | 0.125 |
| Conditioning silicone | 0.5 |
| Dimethicone PEG-8 Phosphate[1] | 0.5 |
| Ammonium Dimethicone PEG-7 Sulfate/AQ[2] | 0.75 |
| Silicone fluids | 0.58 |
| Nonionic surfactant | 1.35 |
| Anionic surfactant | 7.4 |
| Cationic polymer | 0.2 |
| Silicone elastomer aqueous suspension[3] | 0.75 |
| Cationic surfactant | 0.005 |
| Triethanolamine | 0.45 |
| Preservative | 0.2 |
| Fragrance | 0.5 |
| Demineralized Water | QS 100% |

[1]Ultrasil PE-100 available from Noveon, Inc. (100% active)
[2]Ultrasil SA-1 from Noveon, Inc. (35% active)
[3]67% active It should be understood that the foregoing description is only illustrative of the present invention. Various alternatives and modifications can be devised by those skilled in the art without departing from the invention. Accordingly, the present invention is intended to embrace all such alternatives, modifications and variations that fall within the scope of the appended claims.

What is claimed is:

1. A composition for forming a film on hair or skin comprising from about 0.05% to about 20% by weight dimethicone PEG-7 sulfate and from about 0.1% to about 10% by weight diisostearyi polyglyceryl-3 dimer dilinoleate.

2. The composition of claim 1 further comprising dimethicone PEG-8 phosphate.

3. A hair care composition comprising:
(a) one or more anionic silicones selected from the group consisting of dimethicone PEG-7 sulfate, dimethicone PEG-7 phosphate, dimethicone PEG-7 phthalate, dimethicone PEG-7 succinate, dimethicone PEG-8 phosphate, and combinations thereof;
(b) one or more high molecular weight esters selected from the group consisting of diisostearyl polyglyceryl-3 dimer dilinoleate, triisostearoyl polyglyceryl-3 dimer triisostearyl trilinoleate, and combinations thereof;
(c) a hair conditioning agent selected from cationic surfactants and quaternary ammonium compounds; and
(d) a suitable vehicle for said hair care composition;
wherein said anionic silicone comprises from about 0.05% to about 20% by weight of the composition and said high molecular weight esters comprise from about 0.1% to about 10% by weight of the composition.

4. The hair care composition of claim 3 wherein said one or more high molecular weight esters comprises diisostearyl polyglyceryl-3 dimer dilinoleate.

5. The hair care composition of claim 3 wherein the anionic silicone comprises from about 0.1% to about 10% by weight of the composition and the high molecular weight esters comprise from about 1% to about 8% by weight of the composition.

6. A method of treating a hair fiber of the scalp comprising applying to said hair fiber a leave-on hair product comprising: (a) one or more anionic silicones selected from the group consisting of dimethicone PEG-7 sulfate, dimethicone PEG-7 phosphate, dimethicone PEG-7 phthalate, dimethicone PEG-7 succinate, dimethicone PEG-8 phosphate, and combinations thereof; and (b) one or more high molecular weight esters selected from the group consisting di-esters of di-acids or tri-esters of tri-acids having a molecular weight of at least 450; with the provisio that said ester is not diisostearyl.

7. The hair fiber of the scalp or eyelashes according to claim 6, wherein the weight ratio of said one or more high molecular weight esters to said one or more anionic silicones is from about 5:1 to about 1:2.

8. A method of forming a film on a hair fiber comprising applying to said hair fiber a composition comprising:
(1) one or more anionic silicones selected from the group consisting of dimethicone PEG-7 sulfate, dimethicone PEG-7 phosphate, dimethicone PEG-7 phthalate, dimethicone PEG-7 succinate, dimethicone PEG-8 phosphate, and combinations thereof; and
(2) one or more high molecular weight esters selected from the group consisting of diisostearyl polyglyceryl-3 dimer dilinoleate, triisostearoyl polyglyceryl-3 dimer triisostearyl trilinoleate, and combinations thereof;
wherein said anionic silicones comprise from about 0.05% to about 20% by weight of the composition and said high molecular weight esters comprise from about 0.1% to about 10% by weight of the composition.

9. The method of claim 8 wherein said one or more anionic silicones comprises dimethicone PEG-7 sulfate.

10. The method of claim 8 wherein said one or more high molecular weight esters comprises diisostearyl polyglyceryl-3 dimer dilinoleate.

11. The method of claim 8 wherein said one or more anionic silicone comprises from about 0.1% to about 10% by weight of the composition and said one or more high molecular weight esters comprise from about 1% to about 8% by weight of the composition.

12. A method of straightening hair comprising:
(a) wetting said hair;
(b) applying to said wet hair a composition comprising: (i) one or more anionic silicones and (ii) one or more high molecular weight esters having a molecular weight of about 450 or higher selected from the group consisting di-esters of di-acids or tri-esters of tri-acids;
(b) combing or brushing said hair after said composition has been applied; and
(c) drying said hair, optionally by heating said hair;
thereby substantially straightening said hair.

13. The method of claim 12 wherein said hair remains substantially straighter for at least 12 hours following said treatment.

14. The method of claim 12 wherein said hair remains substantially straighter after at least one shampooing or washing.

15. The method of claim 12 wherein said one or more anionic silicones comprises an anionic silicone selected from the group consisting of dimethicone PEG-7 sulfate, dimethicone PEG-7 phosphate, dimethicone PEG-7 phthalate, dimethicone PEG-7 succinate and dimethicone PEG-8 phosphate, and combinations thereof.

16. The method of claim 12 wherein said one or more high molecular weight esters comprise a high molecular weight ester selected from the group consisting of diisostearyl polyglyceryl-3 dimer dilinoleate, triisostearoyl polyglyceryl-3 dimer dilinoleate, diisostearyl dimer dilinoleate, triisostearyl trilinoleate, diisostearyl dimer dilinoleate, and combinations thereof.

17. The method of claim 12 where said one or more anionic silicones comprises dimethicone PEG-7 sulfate and said one or more high molecular weight esters comprise diisostearyl polyglyceryl-3 dimer dilinoleate.

* * * * *